(12) United States Patent
Milsom

(10) Patent No.: US 6,503,219 B2
(45) Date of Patent: ***Jan. 7, 2003

(54) CARDIAC RECOVERY

(75) Inventor: Frederick Paget Milsom, Auckland (NZ)

(73) Assignee: Milsom Holdings Limited (NZ)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/297,540
(22) PCT Filed: Nov. 4, 1997
(86) PCT No.: PCT/NZ97/00150
§ 371 (c)(1),
(2), (4) Date: May 3, 1999
(87) PCT Pub. No.: WO98/19736
PCT Pub. Date: May 14, 1998

(65) Prior Publication Data
US 2002/0062058 A1 May 23, 2002

(30) Foreign Application Priority Data
Nov. 4, 1996 (NZ) ............................................. 299694

(51) Int. Cl.[7] ............................................. A61M 37/00
(52) U.S. Cl. .................. 604/4.01; 604/6.09; 604/6.11; 604/6.14
(58) Field of Search ................................. 604/4.01, 6.1, 604/6.09, 6.11, 6.14, 6.15, 6.16; 600/16

(56) References Cited

U.S. PATENT DOCUMENTS

| 4,961,725 A | 10/1990 | Rey et al. |
| 5,449,342 A | 9/1995 | Hirose et al. |
| 5,814,004 A | * 9/1998 | Tamari ........................... 604/4 |

* cited by examiner

Primary Examiner—Rosiland S. Kearney
(74) Attorney, Agent, or Firm—D. Peter Hochberg; Katherine R. Vieyra; Sean Mellino

(57) ABSTRACT

The apparatus includes a flow control conduit (2) connectable with an output portion of the heart, preferably a bypassed portion of the aorta, and includes a means of feeding heart fluid (R/O), for example blood or cardioplegia into the heart. The flow control device (1) includes in communication a variable resistance pressure control means (4) which is variably biased to a closed position to maintain on the bypassed heart region a predetermined level of pressure, to facilitate the creation of back pressure during filling of the bypassed heart region or a beat or pumping phase of the heart, and when the heart fluid pressure increases to reach a predetermined threshold, the pressure control means facilitates a release of fluid from the conduit, thus facilitating expulsion of potential emboli from the bypassed heart region, and enabling "cycling" of the heart while in a bypassed condition, prior to the bypassed region being taken off bypass. The invention includes preferred and alternative embodiments of variable resistance pressure control means including a hollow deformable bladder (16) biased by a compressible control fluid externally of said bladder.

34 Claims, 6 Drawing Sheets

CARDIAC RECOVERY

Figure 1:
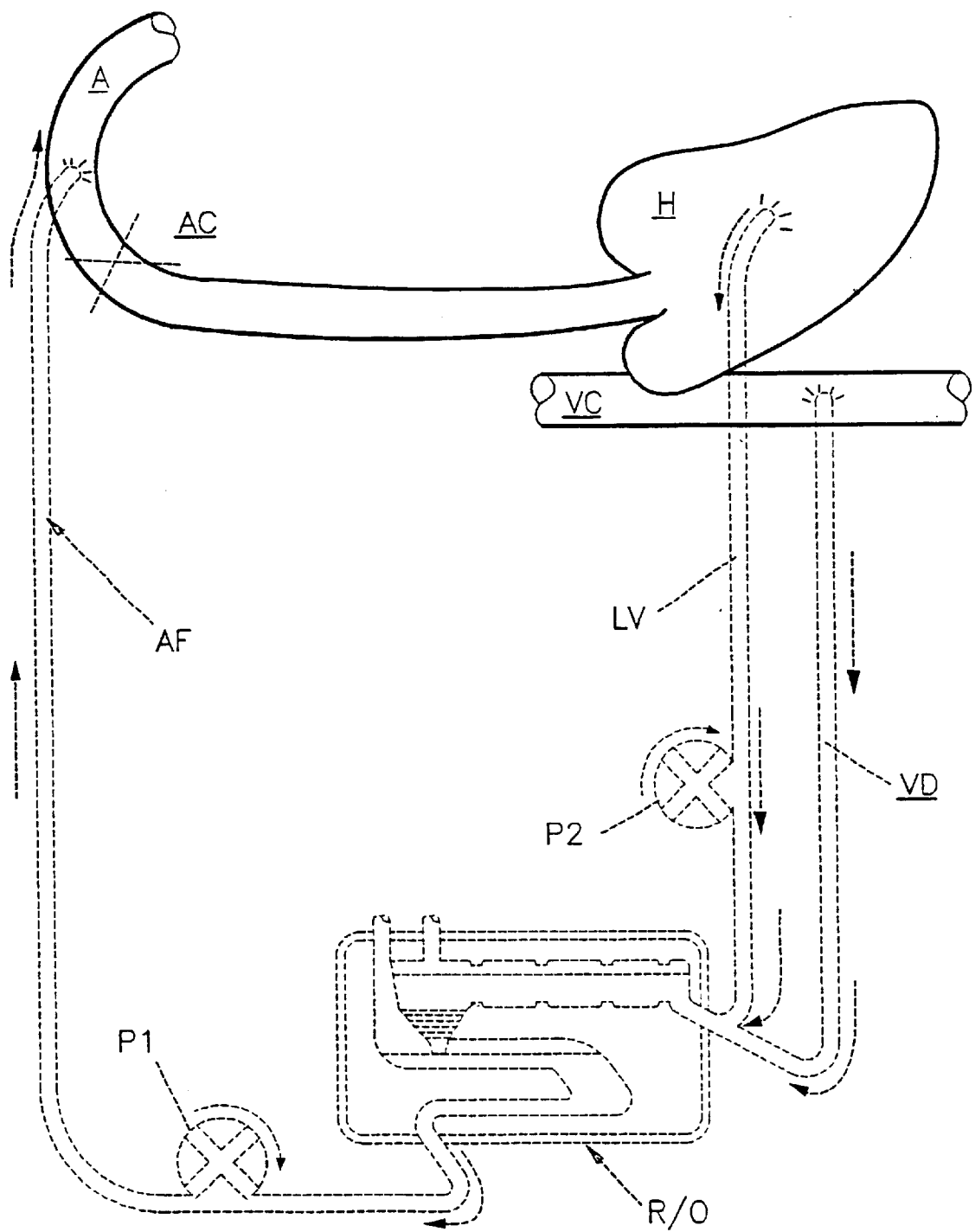

This invention relates to cardiac surgery and more particularly to an apparatus and method of use of such apparatus in cardiac bypass surgery recovery with the aim of minimising dangers of such surgery particularly in the recovery phase.

BACKGROUND TO THE INVENTION

Cardiac surgery, particularly open heart surgery has and remains to be associated with significant risk to the patient, nevertheless there is a trend of incremental developments in surgery techniques and apparatus which tends to reduce risks in the operation.

It has long been recognised, for example by research into the effects of nitrogen narcosis (the bends), gas embolisms and the like manifesting in gas bubble entrainment within the body's vascular system can have adverse effects, such as subsequently impaired brain function or neurocognitive deficits.

It is implicit that in most cases open heart surgery carries with it at least a risk of gas bubble (normally air) and particulate emboli entrainment in the vascular system as a result of the interior of the heart, or the blood vessels associated with the heart becoming punctured, disconnected and open to atmosphere.

In the past, toward completion of a bypass open heart operation, as the surgical repairs are completed, the operating staff undertake various steps in order to "flush" or "bleed" the bypassed region in an endeavour to remove all potential emboli, for example air bubbles, particles and the like from the heart and the associated bypassed vascular system. Such steps have typically included "bleeding" the region via a puncture in the aorta coupled with careful filling of the heart with cardioplegia or blood, aspirating the heart at various positions for example by syringe punctures, coupled with physical manipulation of the heart, for example by squeezing, tilting, suction venting and the like.

Whilst such steps tend to remove most of entrained emboli from the heart and the associated bypassed region, in view of the "cavitied" structure of the heart and associated blood vessels, coupled with the buoyancy of gas bubbles and their tendency to "adhere" to adjacent surfaces, it has been found inevitable that gas bubbles remain in the bypassed region. Tests have shown that despite the most diligent attention to emboli removal, these techniques are not completely effective; at re-instatement of normal circulation by removal of the aortic clamp, gas bubble numbers in the region of 1000 to 5000 at closure of the operation are commonly detected being expelled by the recovered heart and its associated blood vessel system. These bubbles are then transported to the body organs.

OBJECTS OF THE INVENTION

It is an object of this invention to provide an apparatus and/or method of use of such apparatus which at least comes some way in addressing the problems abovenoted, or at least provide the public with a useful choice.

Other objects of this invention will become apparent from the following description.

BROAD DESCRIPTION OF THE INVENTION

According to one aspect of this invention there is provided a fluid control device adapted for communication with a fluid supply, said flow control device including a pressure control means adapted to control a fluctuating fluid pressure in said device wherein said pressure control means is normally biased toward a closed position for maintaining a predetermined level of upstream backpressure, but is openable under the bias under predetermined additional pressure to release fluid from said fluid control device, said pressure control means providing a bias which is proportional to an extent of opening of said pressure control device and the predetermined additional pressure.

According to a further aspect of this invention there is provided a fluid control device adapted for connection in controlled communication with a bypassed heart region, and a heart fluid supply for said bypassed heart region, said fluid control device including a variable resistance pressure control means adapted to control heart fluid flow from, and/or fluctuating pressure in, said bypassed heart region, said pressure control means including an opening in communication with said bypassed heart region normally biased toward a closed position for maintaining a predetermined level of upstream backpressure, but variably openable against the bias under predetermined additional heart fluid pressure in said bypassed heart region to release through said opening heart fluid from said bypassed region, said pressure control means providing a bias which is proportional to a cross-sectional area of the opening in said pressure control means and the predetermined additional heart fluid pressure in said bypassed heart region.

According to a still further aspect of this invention there is provided a method of improving the removal of potential emboli from a bypassed heart region prior to removal of said region from bypass including the steps of connecting a fluid control device in communication with an output portion of said bypassed heart region, said fluid control device having a variable resistance pressure control device in communication with said bypassed heart region capable of releasing heart fluid from said fluid control device over a predetermined pressure, filling said bypassed heart region with heart fluid and allowing said heart to pump said heart fluid whilst in a bypassed condition, and whilst maintaining an inflow of heart fluid to said bypassed heart region.

According to a still further aspect of this invention there is provided a system for reducing potential emboli from a bypassed heart region prior to removal of said region from bypass, a fluid control device adapted for connection in controlled communication with a bypassed heart region and a heart fluid supply for said bypassed heart region, said fluid control device including a variable resistance pressure control means adapted to control a heart fluid flow from and/or pressure in said bypassed heart region, said pressure control means normally biased towards a closed position, but openable against the bias under predetermined heart fluid pressure in said bypassed heart region to release heart fluid from said bypassed heart region, said pressure control means providing a bias which is proportional to cross-sectional area of an opening in said pressure control means and heart fluid pressure in said bypassed heart region.

According to a still further aspect of this invention there is provided a fluid control device including a conduit assembly connectable for controlled communication with a bypassed heart region and a venous line of a body vascular system including a variable resistance pressure control means variably biased to a normally closed position for maintaining a predetermined level of upstream backpressure and openable under additional predetermined aortic heart fluid pressure to at least partially control fluctuating heart fluid pressure in the bypassed heart region, said fluid control device connectable with a fluid reservoir and/or oxygenation device for circulation of heart fluid between said bypassed heart region and said fluid reservoir and/or oxygenation device whilst said bypassed heart region is at least partially bypassed, said pressure control means adapted to control the fluctuating heart fluid pressure in said at least partially bypassed heart region during heart filling and subsequent heart pumping; where said heart moves heart fluid in said bypassed portions of said heart during a recovery period, prior to completion of removal of said bypassed heart region from the bypassed condition.

Other aspects of this invention which should be considered in all its novel aspects will become apparent from the following description. Modifications are envisaged and may be incorporated without departing from the scope or spirit of the invention.

DESCRIPTION OF THE PREFERRED EMBODIMENT

The preferred form of the invention will now be described with reference to the accompanying drawings in which:

FIG. 1. is a substantially diagrammatic view of a typical traditional bypass circulatory system used when conducting heart bypass surgery.

Figure 2:
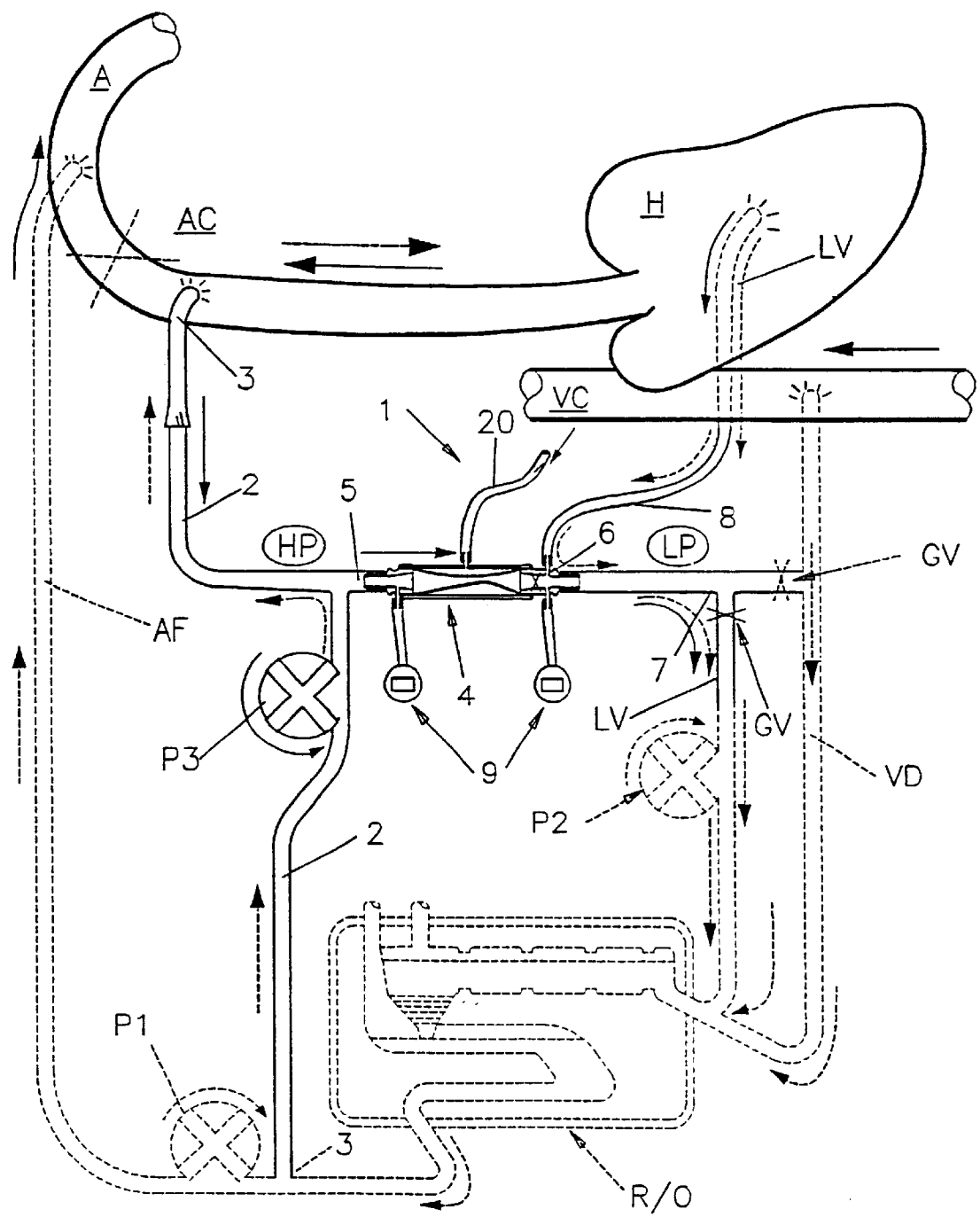

FIG. 2. is a similar view to FIG. 1, however showing the apparatus of this invention and its method of use in bypass heart surgery.

Figure 3:
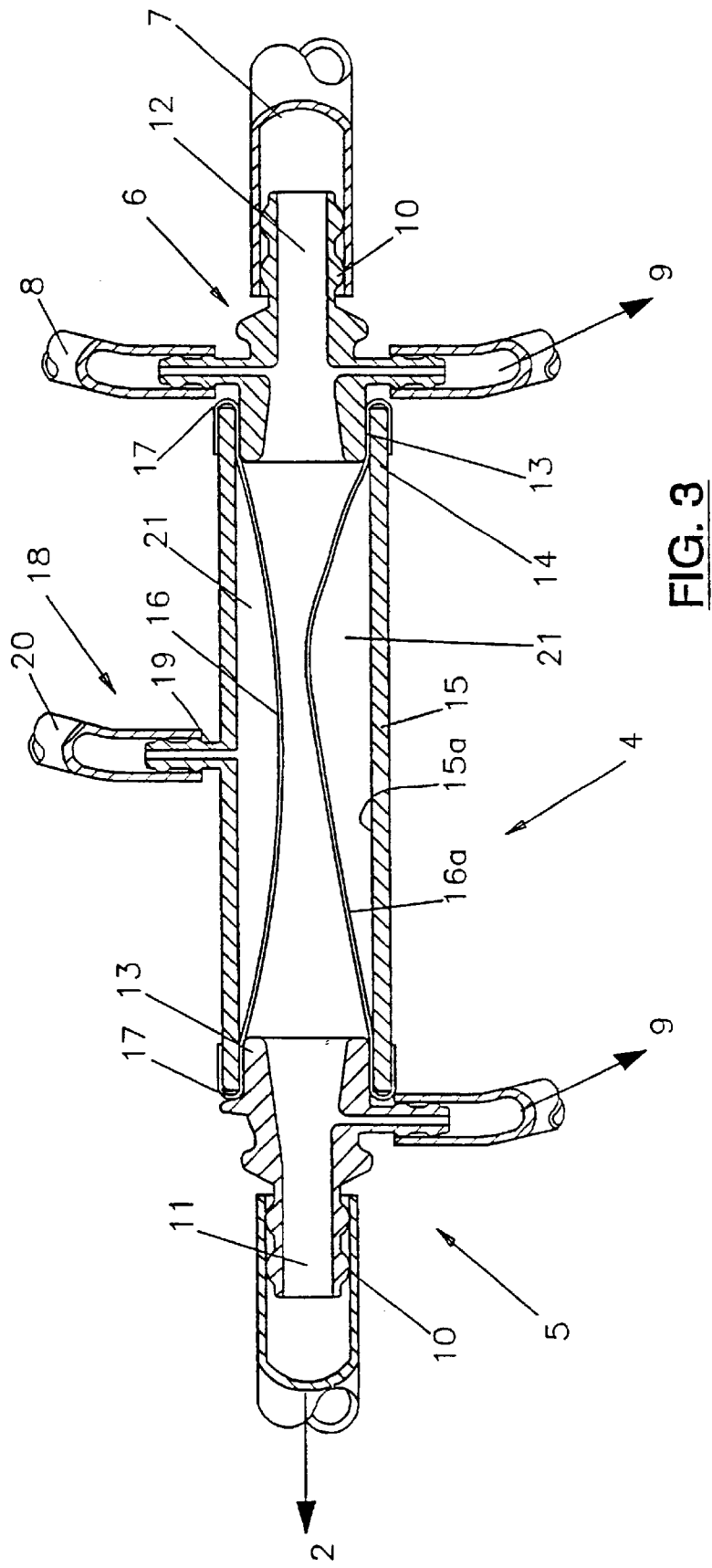

FIG. 3. is a substantially diagrammatic cross-sectional side elevation of a preferred pressure control means according to the invention.

Figure 4:
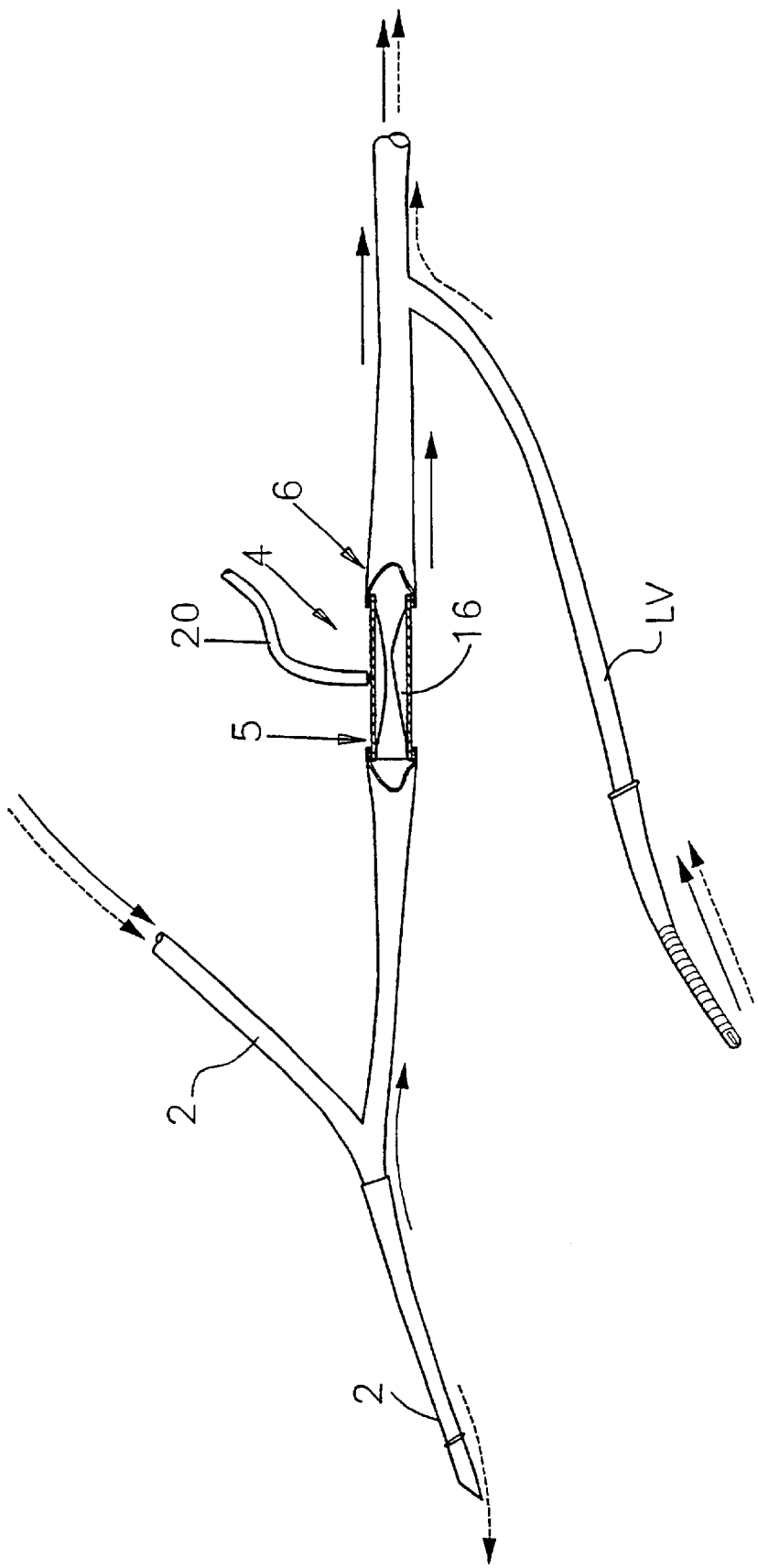

FIG. 4. is an assembly drawing of a typical fluid control device of this invention showing the variable resistance flow control means in partial cutaway form.

Figure 5:
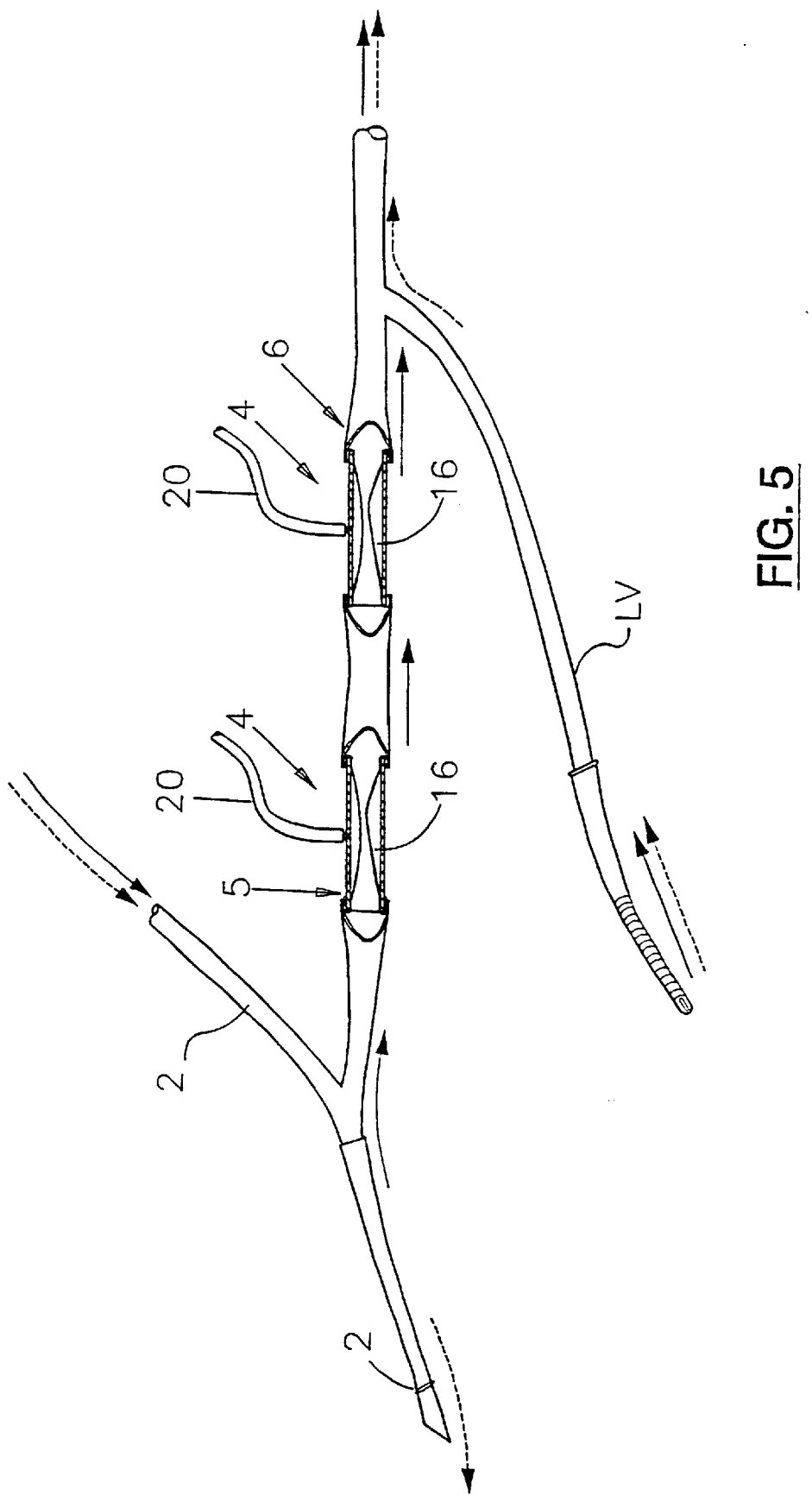

FIG. 5. is an assembly drawing of a further embodiment of the a typical fluid control device of FIG. 4 of this invention showing the variable resistance flow control means in partial cutaway form.

Figure 6:
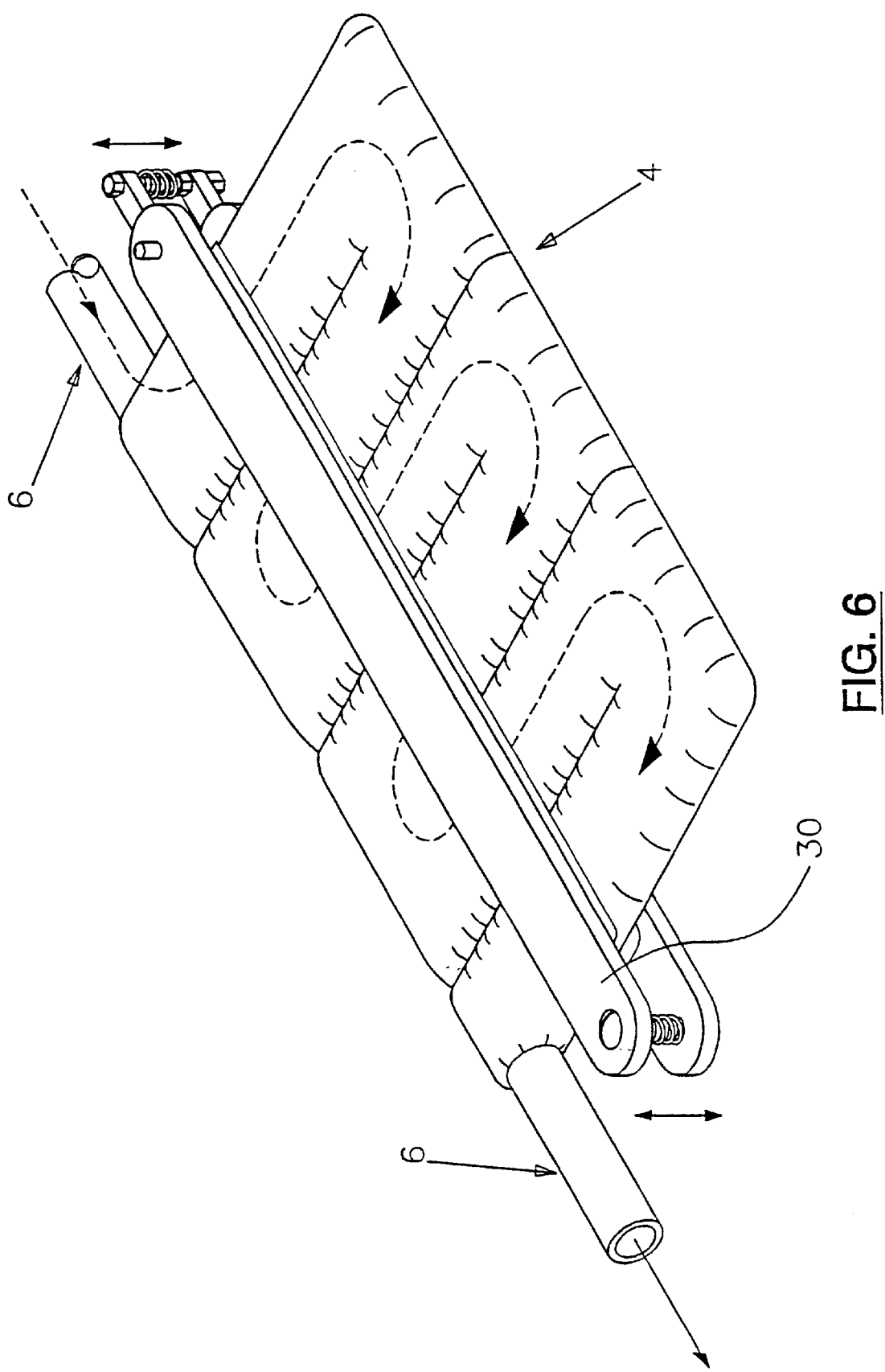

FIG. 6. is a substantially diagrammatic side view of a pressure control means according to an alternative embodiment of the invention.

DETAILED DESCRIPTION

The preferred form of the invention is also described with reference to a paper headed "A Novel Dual Vent Left Heart De-Airing Technique Markedly Reduces Carotid Artery Micoemboli After Valve Surgery" by the inventor F P Milsom FRACS (unpublished).

Referring generally to the drawings, it will be appreciated that FIGS. 1 and 2 show substantially diagrammatically in disposition a normal heart bypass assembly configuration, although this configuration can vary in certain circumstances. It is to be assumed that the heart H, aorta A and vena cavae V are substantially in a disposition of that of a patient undergoing open heart surgery.

An aortic clamp AC is shown diagrammatically at a portion of the aorta remote from the heart H and is in the substantially traditional form.

Venous blood from the body vascular system is drawn off the vena cavae VC or alternatively, the right atrium (not shown), via a gravity venous drain engaged through a predetermined puncture in the vena cavae VC or right atrium, leading to a reservoir/oxygenation apparatus R/O of substantially known construction. The reservoir/ oxygenation apparatus R/O also provides for de-bubbling or de-aeration and reoxygenation of the blood prior to it being returned to the body vascular system via a pump P1 for example a roller pump and an aortic feed AF line which terminates in the aorta A downstream of the aortic clamp on a side of the aortic clamp AC remote from the heart H.

In addition to the venous drain VD frequently a further left ventricular drain LV extends from insertion from the heart H left ventricle (not shown), to the inlet side of the reservoir/oxygenator apparatus R/O preferably via a second pump P2. In this way it will be appreciated that blood flow through the heart H and the associated blood vessels can be bypassed to enable open heart surgery.

Referring to FIGS. 2 and 3 in particular, and also FIGS. 4 and 5, it will be appreciated that in FIGS. 1 and 2 the "normal" bypass assemblies are shown in broken lines whereas in FIG. 2, the apparatus of this invention is shown in solid lines (with the exception of the diagrammatic representation of the heart H, aorta A and vena cavae VC).

The apparatus is formed in suitable materials including appropriately graded plastic materials, metals and the like, although the invention is not limited to such materials and alternative suitable materials may be provided.

With reference to FIG. 2, the apparatus as generally indicated by arrow 1 include an arterial line 2 preferably formed in suitable flexible pipework material, which is arranged at an inlet end 3 to couple, for example by a suitable T or Y connector or the like (not shown), with an outlet portion of the reservoir and oxygenator R/O, such that oxygenated blood, or alternatively cardioplegia can be supplied to the arterial line 2.

A pump P3 is provided on the arterial line, for example a suitable roller pump or the like, to provide fluid flow through the line 2 at a predetermined flow and pressure rate. The arterial line 2 terminates in communication with the aorta, preferably via a predetermined puncture through the aortic wall upstream of the aortic clamp AC, such that on operation of the pump P3, blood and/or cardioplegia, can be supplied to the aorta and via the aorta the heart in a controlled manner to allow for use of line 2 throughout procedure and preferably during recovery of the heart H after surgery.

The arterial supply line 2 is also arranged in communication with a pressure control valve adapted to provide a variable resistance to fluid flow in the arterial supply line 2. The pressure control valve 4 as depicted in FIGS. 2 and 3 is a preferred form of such a valve, however, in alternative forms of the invention alternative pressure control valves can be utilised with the apparatus of this invention.

The pressure control valve 4 in the preferred form of the invention has an intended high pressure side 5 connected, for example by suitable fittings, pipework and the like with the arterial supply line 2. The pressure control means 4 is preferably variably adjustable in its resistance and is controllable to provide a closed position, yet is able to open against a bias on a preferably progressive basis, dependent on the pressure found in the arterial supply line 2 upstream at the valve, thus the pressure control means 4 provides in effect a variable resistor.

An intended low pressure side 6 of the pressure control means 4 provides a return line 7 preferably in the form of a conduit coupled with the intended low pressure side 6 of the pressure control means 4 and in communication via suitable pipework, for example a T or Y connector and the like with the venous drain VD.

The apparatus, preferably but not essentially also includes a left ventricular drain 8 which is also in communication with the intended low pressure side 6 of the pressure control means 4. In the preferred form of the invention, preferably in use, the left ventricular drain LV as shown in FIG. 1 (and also FIG. 2 in varied form) is controlled by gate valves generally indicated by arrows GV, for coupling of the left ventricular drain LV to the intended low pressure side 6 and "in circuit" to the reservoir and/or oxygenator device R/O.

Suitable monitoring apparatus 9 are preferably provided for monitoring pressure within the arterial supply line 2 and on the low pressure side 6 of the assembly. Preferably such monitoring arrangements include electronic display apparatus and also optionally include interactive and response initiating apparatus dependent on predetermined criteria, controlled by use of integrated circuits such as comparators and the like.

Referring to FIG. 3 in particular, it will be appreciated that in the preferred form of the invention, the pressure control means 4 in the preferred form of the invention is adapted for use in the apparatus and for coupling with remaining portions of the apparatus in a suitable spigot/socket arrangement, incorporating appropriate clamps and the like. The pressure control apparatus 4 is provided with a pair of end portions, preferably moulded in suitable plastics materials and the like incorporating an inlet bore 11 in the case of the intended high pressure of the apparatus and an outlet bore 12 in the case of the intended low pressure side 6.

Each of the fittings 10 are provided with an inner-spigot 13 is provided of a substantially friction tight fit with an open end portion 14 of a housing 15. Preferably the housing 15 and associated spigot portions 13 are of substantially round or annular cross-section, although this is in no way essential to the invention and in the preferred form of the invention, preferably the body portion is formed of a substantially clear plastics material so as to enable vision therethrough.

The pressure control means 4 is formed in suitable materials in a substantially unitary structure, for example incorporating the housing 15 and bladder portions conjoined with one another, for example by radio frequency welding, solvent gluing or bimoulding and the like, such that the apparatus is formed in an integral unit, or a substantially integral unit and in a way which is convenient for economic production and convenient disposability of the unit after use.

A deformable bladder member 16 is, in the preferred form of the invention, provided to engage within the housing 15 and between the fittings 10. In the preferred form the bladder member 16 is formed of relatively thin and pliable material, for example clinical grade elastic silicone, PVC, or other flexible or elastomeric materials and in a substantially tubular configuration of a diameter that, in a relaxed state, outer surfaces 16a are able to lie substantially in juxtaposition with interior faces 15a of the housing 15 and where end portions 17 of the bladder 16 are able to flare outwardly about ends of the housing 15, to terminate in portions engaged snugly about exterior surfaces of the housing end portions 14.

It will be appreciated that by frictional engagement of these end fittings 10 spigots 13 in the housing end portions 14, portions of the bladder are sandwiched therebetween, to create a convenient and fluid tight seal and furthermore, to provide a variable conduit through the valve 4 from the inlet bore 11 to the outlet bore 12 which is readily able to be assembled in a sterile form yet which is substantially mechanically robust; while a friction fit is disclosed as a preferred option, it will be appreciated that the assembly could be subject to gluing or welding as an alternative.

The housing 15 in the preferred form of the invention incorporates a control assembly as generally indicated by 18 and preferably includes a spigoted port 19 which passes through the housing 15 wall to enable connection of a control conduit 20 therewith. The port 19 in some cases can be also provided with a non-return valve (not shown).

It will appreciated that cross-sectional area of the available passageway through the pressure control means 4 can be varied according to the extent of control fluid which fills a chamber 21 which can be established by control fluid being pumped into the chamber 21 via the control conduit 20.

Although this is in no way essential to the invention, the control fluid used for the chamber 21 is a compressible gas, however in alternative forms of the invention, other fluids can also be utilised, subject to appropriate pressure control apparatus being provided.

It is envisaged that in one embodiment there will be an interconnection between the control fluid volume and/or pressure applied to the chamber 21 and the detected pressure within one or both of the arterial supply line or parts of the assembly on the low pressure side 6 of the pressure control means 4.

Alternatively, it is envisaged that the pressure/volume of control fluid for the chamber 21 can be influenced by other pressure and/or flow rates within the apparatus or the heart H, the aorta or elsewhere in the body vascular system.

It should be understood that in alternative embodiments of the invention and as shown in FIG. 5 a "smoothing" of flow through the arterial supply line 2 upstream of the pressure control valve 4 can be achieved by mounting a number of pressure control valves 4 in communication in series with a small reservoir therebetween. In this way, it will be appreciated that a flow resistance can be reduced over a single valve assembly 4 as previously described where a pressure gradient between control fluid in the chamber 21 and the passageway or opening through the deformable bladder member 16 is reduced, thus enabling pressure to be maintained on the arterial supply line 2 and the bypassed heart region sufficient to provide perfusion of the tissue in the bypassed heart region during a rest phase yet maintaining relatively little resistance to flow when the passageway through the bladder 16 opens under increased heart pumping pressure during a pumping phase.

In a further alternative embodiment of the invention and as shown in FIG. 6, a further alternative arrangement for "smoothing" of flow through the arterial supply line 2 to upstream of the pressure control valve can be achieved by providing an alternative assembly of pressure control means as generally indicated by arrow 4 which is preferably formed as a flexible envelope formed from flexible sheet material to define a serpentine labyrinth passageway between the intended high pressure side 5 and the intended low pressure side 6.

A controllable variable clamping means 30 is arranged for clamping across the flexible envelope to provide a variable clamping action on the envelope, to have the effect of variably restricting the labyrinth passageway.

It is intended in this form of the invention that the envelope be provided, for example in suitable plastics sheet material suitably welded together, for example by fusion welding and the like to achieve the structure in an economical, sterile manner as appropriate to the conditions of use.

The abovementioned alternative embodiments of pressure control arrangements are intended to closely approximate a natural pressure and operational situation for the heart.

Use of the apparatus 1 according to the invention is intended as an integrated assembly such as that depicted in FIGS. 4 or 5 connected into the bypass equipment as shown diagrammatically in FIG. 2, as the open heart surgery operation is reaching a conclusion and where the heart H is required to be resuscitated.

Preferably installation of the apparatus 1 assembly is done partially, at commencement of the bypass procedure, in conjunction with such bypass procedure, or alternatively immediately prior to heart resuscitation at conclusion of the surgical procedures phase. At substantial completion of the surgical procedures on the bypassed region the heart H is resuscitated, flushed with cardioplegia and subsequently arterial blood simultaneously with continuation of the normal by separate bypass blood circulation.

In the preferred operation, suitable valving/pump/supply connections (not shown) enabling supply of cardioplegia and blood to the arterial supply line 2 and the pump P3 is operated to infuse the heart H via the portion of the aorta A upstream of the aortic clamp AC as shown by broken flow lines in FIG. 2. The effect of filling the heart H in this way enables the surgeon to manipulate the heart and to remove significant quantities of mixed fluids, for example gases and particles and other emboli and begin the heart H resuscitation process.

It will be appreciated that upon the heart H and associated bypass vessels filling, such portions will be substantially protected from undue dilation by the pressure control means 4 which, having been previously set to a predetermined and possibly variable pressure remains closed, until such time as such predetermined pressure is reached. This pressure threshold is reached, for example by pump 3 pressure or alternatively, by pressure on the heart H starting to beat, and controls the pressure on the heart H and bypassed region through discharge of sufficient cardioplegia blood from the arterial supply line 2 through the pressure control means 4 a pressure in excess of a predetermined pressure be encountered therein. Blood/cardioplegia flow on heart H beat pumping is shown by solid flow lines of FIG. 2.

The pressure control means 4 constructed in the arrangement described, by virtue of the bias created on the bladder 16 facilitates the creation of "backpressure", in the apparatus and thus in the bypassed heart region, and during filling of the heart or a beat or pumping phase of the heart, it is only when the heart fluid pressure increases to reach a predetermined threshold that a flow of heart fluid through the pressure control means 4 occurs; the extent or volume of that flow being controlled by the variable resistance created by the valve means in proportion to the additional pressure created. The cross-sectional area of the opening or passageway through the bladder 16 is thus proportional to the additional created pressure over the predetermined threshold; this environment approximates a natural situation for the heart.

In an alternative arrangement, it is anticipated that the pressure at which the control means 4 releases pressure, can be varied, according to an automatic, such as "feedback control" from pressure within the remaining parts of the apparatus 1, or alternatively, by way of control by sensors placed at strategic and predetermined positions in the downstream portion of the bypassed region, or the heart H.

As the heart H commences to beat, it will be appreciated that the heart H can pump through a circuit upstream of the aortic clamp AC and through the reservoir/oxygenation apparatus R/O, effectively reversing the blood flow through the portion of the arterial supply line 2 downstream of the pump, but upstream of the pressure control means 4, thus enabling the heart H to pump while the aortic clamp AC is closed, until such time as the surgeon is satisfied that all potential emboli, for example gas bubbles or particles which would otherwise have been entrained within the heart H and associated bypassed region have been removed by the heart H pumping action and furthermore, that in all other aspects the patient can come "off" bypass.

Upon the above-mentioned happy situation having been reached, the surgeon is then able to release the aortic clamp AC to enable natural aortic blood flow and then attend to removal of the apparatus 1 and the bypass apparatus, prior to completion of other aspects of the operation.

It will be appreciated that in view of the manner in which the chamber 21 of the pressure control valve 4 is filled in the preferred form of the invention with a compressible gas, a restriction provided by the pressure control means is variable, proportionately to the pressure on the bladder 16 on the normally high pressure side 5, such that as the heart H begins to resuscitate and subsequently increases in strength and pumping capacity the volumetric capacity of the passageway through the bladder and thus the level of restriction is reduced; enabling circulation of blood/cardioplegia possibly containing potential emboli and subsequent non-potential emboli containing blood independently of the bypassed normal body vascular system.

It will be appreciated that the pressure control means 4 provide resistance against which the heart can pump, with the flow rate and pressure being proportional. In this way, the bias of the pressure control means 4 can be adjusted to maintain a sufficient predetermined rest state pressure in the arterial line 2 which facilitates perfusion of the bypassed heart region and which can approximate a normal environment against which the heart normally pumps together with relatively low resistance to flow on the heart beat pumping action of the heart.

Whilst the invention has been described with reference to a particular type of pressure control means, it is to be understood that the invention is not limited to such a pressure control device 4.

Furthermore, whilst the pressure control device 4 described is shown as a pressure control means and/or restrictor for cardiac recovery means, it is envisaged that the valve/ restrictor apparatus may also have alternative applications, particularly but not exclusively where the construction and arrangement facilitating convenient sterilisation and promotion of sterile conditions is required.

It will be appreciated that the substantially "automatic" variation of control of blood pressure and flow rate, conveniently enables de-aeration of the bypassed portions without the need for direct attention of the surgeon at a time when it may well be diverted elsewhere, such as ensuring that other operative work is holding up and that the patient's vital signs are returning.

It will appreciated that in certain circumstances, the ability for the pressure control means to fluctuate the extent of restriction and thus the flow rate and pressure, actively, in response to predetermined criteria and/or sensors, such as the monitoring apparatus 9 described with reference to FIG. 2 further may enable the surgeon's attention to be safely diverted elsewhere.

Thus by this invention there is provided an apparatus for cardiac recovery and/or a method of use of such apparatus which facilitates improved patient safety and improved quality of cardiac recovery in bypass surgery.

The invention has been described in detail with particular emphasis on the preferred embodiment, but variations and modifications within the spirit and scope of the invention may occur to those skilled in the art from the foregoing disclosure and from the appended claims.

What is claimed is:

1. A fluid control device for use with a bypass circulatory system, the bypass circulatory system including a reservoir/oxygenation apparatus between the venous and arterial sides of the bypass circulatory system, the fluid control device including:
   (a) a first communication apparatus to allow heart fluid flow from a bypassed section of the aorta to the venous side of the bypass circulatory system via a variable resistance pressure control device; and
   (b) a second communication apparatus consisting of an arterial supply line to allow heart fluid flow from the arterial side of the bypass circulatory system to the bypassed section of the aorta; wherein the first and second communication apparatus share a portion of the arterial supply line of the second communication apparatus adjacent and connecting to the bypassed section of the aorta.

2. A fluid control device as claimed in claim 1 wherein said fluid control device is arranged to act in use as a conduit for controlled communication between the bypassed heart region and a supply of heart fluid to facilitate flushing and/or operation of the bypassed heart region while at least partially bypassed, and wherein said variable resistance pressure control device is adapted to control the heart fluid pressure in the at least partially bypassed heart region and the fluid control device.

3. A fluid control device as claimed in claim 1 where the bypassed heart region is supplied with heart fluid via the second communication apparatus.

4. A fluid control device as claimed in claim 1 wherein the variable resistance pressure control device includes at least one inlet and at least one outlet in communication via a housing, a deformable hollow bladder forming moveable portions in communication with said inlet and said outlet within the housing providing the opening capable of carrying heart fluid flow passing from said inlet to said outlet, at least a portion of said deformable bladder compressible by control fluid pressure impinging on an exterior of said deformable bladder to control heart fluid flow therethrough.

5. A fluid control device as claimed in claim 4 wherein the extent of bias provided by the variable resistance pressure control device is variable by varying the pressure of said control fluid.

6. A fluid control device as claimed in claim 5 wherein the deformable hollow bladder is engaged within said housing to pass through a cavity of said housing with at least one end portion thereof flared outwardly and engaged about that end portion in a substantially opposite manner to remaining portions of said housing.

7. A fluid control device as claimed in claim 6 wherein the deformable hollow bladder is engaged with end portions thereof sandwiched between adjacent portions of end portions of said housing and connection means inserted within said housing and portions.

8. A fluid control device as claimed in claim 1 wherein the bias of the variable resistance pressure control device maintains a predetermined minimum heart fluid pressure in said bypassed heart region, sufficient to achieve at least partial perfusion of tissue in the bypassed heart region.

9. A fluid control device as claimed in claim 1 including at least two substantially independently operable variable resistance pressure control means interconnected in series.

10. A fluid control device as claimed in claim 1 wherein the variable resistance pressure control device includes a flexible portion defining a fluid passageway therein which transits a clamping device adapted for controlling a cross-sectional area of said passage-way, and thus flow of fluid through said pressure control apparatus.

11. A fluid control device for use with a bypass circulatory system, the bypass circulatory system including a reservoir/oxygenation apparatus between the venous and arterial sides of the bypass circulatory system, the fluid control device including:
   (a) a first communication apparatus to allow heart fluid flow from a bypassed section of the aorta to the venous side of the bypass circulatory system via a variable resistance pressure control device; and
   (b) a second communication apparatus consisting of an arterial supply line to allow heart fluid flow from the arterial side of the bypass circulatory system to the bypassed section of the aorta; wherein the first and second communication apparatus share a portion of the arterial supply line of the second communication apparatus adjacent and connecting to the bypassed section of the aorta allowing heart fluid flow to and from the bypassed section of the aorta in the shared portion of the arterial supply line in response to changes in heart fluid flow direction.

12. A fluid control device for use with a bypass circulatory system, the bypass circulatory system including a reservoir/oxygenation apparatus between the venous and arterial sides of the bypass circulatory system, the fluid control device including:
   (a) a first communication apparatus to allow heart fluid flow from a bypassed section of the aorta to the venous side of the bypass circulatory system via a predetermined pressure control device; and
   (b) a second communication apparatus consisting of an arterial supply line to allow heart fluid flow from the arterial side of the bypass circulatory system to the bypassed section of the aorta; wherein the first and second communication apparatus share a portion of the arterial supply line of the second communication apparatus adjacent and connecting to the bypassed section of the aorta.

13. The fluid control device of claim 12 wherein the output portion of the bypassed heart region is a singular opening in the aorta which allows heart fluid flow into and out of the bypassed heart region.

14. A fluid control device for use with a bypass circulatory system, the bypass circulatory system including a reservoir/oxygenation apparatus between the venous and arterial sides of the bypass circulatory system, the bypass system establishing a bypassed section of an aorta, the fluid control device including:
   (a) a first communication apparatus comprising an arterial supply line adjacent to said bypass circulatory system having a portion connected to the aorta at the bypassed section, and a variable resistance pressure control device interconnecting said arterial supply line and the venous side of the bypass circulatory system to allow heart fluid flow from the bypassed section of the aorta to the venous side of the system, said variable resistance pressure control device varying the flow of heart fluid through the arterial supply line according to a control pressure; and
   (b) a second communication apparatus comprising said arterial supply line interconnecting the arterial side of the bypass circulatory system to the bypassed section of the aorta to allow heart fluid flow from the arterial side to the bypassed section thereby providing for bidirectional flow through the portion of said arterial supply line connected to the aorta.

15. A fluid control device as claimed in claim 14 wherein the bypassed section of the aorta is part of a bypassed heart region and wherein said fluid control device comprises a conduit for controlled communication between the bypassed heart region and a supply of heart fluid to facilitate flushing and/or operation of the bypassed heart region while at least partially bypassed, and wherein said variable resistance pressure control device is adapted to control the heart fluid pressure in the at least partially bypassed heart region and the fluid control device.

16. A fluid control device as claimed in claim 14 where the arterial supply line of said second communication apparatus supplies heart fluid to the bypassed heart region.

17. A fluid control device as claimed in claim 14 wherein the variable resistance pressure control device includes at least one inlet and at least one outlet in communication via a housing, a deformable hollow bladder forming moveable portions in communication with said inlet and said outlet within the housing providing the opening capable of carrying heart fluid flow passing from said inlet to said outlet, wherein the control pressure is control fluid pressure applied to said variable resistance control device, and wherein at least a portion of said deformable bladder being compressible by the control fluid pressure impinging on an exterior of said deformable bladder to control heart fluid flow therethrough.

18. A fluid control device as claimed in claim 17 wherein the variable resistance pressure control device provides a bias by modifying the pressure of the heart fluid in accordance with the value of the control fluid pressure.

19. A fluid control device as claimed in claim 17 wherein the deformable hollow bladder is engaged within said housing to pass through a cavity of said housing with at least one end portion thereof flared outwardly and engaged about that end portion in a subsequently opposite manner to remaining portions of said housing.

20. A fluid control device as claimed in claim 17 wherein the deformable hollow bladder is engaged with end portions thereof sandwiched between adjacent portions of end portions of said housing and connection means inserted within said housing and portions.

21. A fluid control device as claimed in claim 14 wherein the control pressure effects a bias on the variable resistance pressure control device to maintain a predetermined minimum heart fluid pressure in said bypassed heart region, sufficient to achieve at least partial perfusion of tissue in the bypassed heart region.

22. A fluid control device as claimed in claim 14 wherein said variable resistance pressure control device comprises at least two substantially independently operable variable resistance pressure control means interconnected in series.

23. A fluid control device as claimed in claim 14 wherein the variable resistance pressure control device includes a flexible portion defining a fluid passageway therein which transits a clamping device adapted for controlling a cross-sectional area of said passage-way, and to thereby control the flow of fluid through said pressure control apparatus.

24. A fluid control device for use with a bypass circulatory system, the bypass circulatory system including a reservoir/oxygenation apparatus between the venous and arterial sides of the bypass circulatory system, the bypass circulatory system establishing a bypassed section of an aorta, the fluid control device including:
(a) a first communication apparatus comprising an arterial supply line adjacent to said bypass circulatory system having a portion connected to the aorta at the bypassed section, and a variable resistance pressure control device interconnecting said arterial supply line and the venous side of the bypass circulatory system to allow heart fluid flow from the bypassed section of the aorta to the venous side of the system, said variable resistance pressure control device varying the flow of heart fluid through the arterial supply line according to a control pressure; and
(b) a second communication apparatus comprising said arterial supply line interconnecting the arterial side of the bypass circulatory system to the bypassed section of the aorta to allow heart fluid flow from the arterial side to the bypassed section thereby providing for bidirectional flow through the portion of said arterial supply line connected to the aorta, wherein the first and second communication apparatus share a portion of the arterial supply line of the second communication apparatus adjacent and connecting to the bypassed section of the aorta, thereby allowing heart fluid flow to and from the bypassed section of the aorta in the shared portion of the arterial supply line in response to changes in heart fluid flow direction.

25. A fluid control device for use with a bypass circulatory system, the bypass circulatory system including a reservoir/oxygenation apparatus between the venous and arterial sides of the bypass circulatory system, the fluid control device including:
(a) a first communication apparatus comprising an arterial supply line adjacent to said bypass circulatory system having a portion connected to the aorta at the bypassed section, and a predetermined pressure control device interconnecting said arterial supply line and the venous side of the bypass circulatory system to allow heart fluid flow from the bypassed section of the aorta to the venous side of the system, said predetermined pressure control device varying the flow of heart fluid through the arterial supply line according to a control pressure; and
(b) a second communication apparatus comprising said arterial supply line interconnecting the arterial side of the bypass circulatory system to the bypassed section of the aorta to allow heart fluid flow from the arterial side to the bypassed section thereby providing for bidirectional flow through the portion of said arterial supply line connected to the aorta, wherein the first and second communication apparatus share a portion of the arterial supply line of the second communication apparatus adjacent and connecting to the bypassed section of the aorta.

26. The fluid control device of claim 25 wherein heart fluid flow into and out of the bypassed heart region at the output portion of the bypassed heart region is defined by a supply line that enters the aorta through a singular opening in the aorta.

27. A method of improving the removal of potential emboli and/or other material from a bypassed heart region prior to removal of said region from bypass, said method including enabling the supply of heart fluid to the bypassed heart via a bypassed portion of the aorta, upstream of an aortic clamp, applied to the aorta with the bypass circulatory system still operating, controlling heart fluid pressure in the bypassed heart region by a variable resistance pressure control device in communication with the bypassed heart region and capable of releasing heart fluid from that region at a predetermined pressure, and manipulating the heart to remove gases, particles and/or emboli and induce heart resuscitation with the bypass circulatory system still operating.

28. A method as claimed in claim 27 wherein the supply of heart fluid to and release of heart fluid from the bypassed heart region is via a singular opening in the bypassed portion of the aorta.

29. A method of improving the removal of potential emboli from a bypassed heart region prior to removal of said region from bypass including the steps of:
 (a) connecting a fluid control device in a bypass circulatory system, said fluid control device including a variable resistance pressure control device, a first communication apparatus interconnecting said variable resistance pressure control device to high and low pressure sides of the bypass circulatory system, and a second communication apparatus interconnecting the variable resistance pressure control device to the bypassed heart region, and enabling communication between the high pressure side of the bypass circulatory system with the bypassed heart region, and wherein said variable resistance pressure control device is normally biased towards a closed position for maintaining a predetermined additional heart fluid pressure in the bypassed heart region;
 (b) filling the bypassed heart region with heart fluid via said second communication device; and (c) allowing said heart to pump said heart fluid whilst in an at least partially bypassed condition.

30. A method as claimed in claim 29 wherein the fluid control device is. communication with the bypassed heart region via a singular opening is bypassed section of the aorta.

31. A method of improving the removal of potential emboli from a bypassed heart region prior to the removal of said region from bypass including the steps of connecting a fluid control device in communication with an output portion of said bypassed heart region, said fluid control device having a variable resistance pressure control device in communication with said bypassed heart region capable of releasing heart fluid from said fluid control device over a predetermined pressure, filling said bypassed heart region with heart fluid and allowing said heart to pump said heart fluid whilst in a bypassed condition, and whilst maintaining an inflow of heart fluid to said bypassed heart region.

32. A method as claimed in claim 31 wherein the output portion of the bypassed heart region is a singular opening in the aorta which allows heart fluid flow into and out of the bypassed heart region.

33. A method of improving the removal of potential emboli from a bypassed heart region prior to the removal of said region from bypass including the steps of connecting a fluid control device in communication with an output portion of said bypassed heart region, said fluid control device having a predetermined pressure control device in communication with said bypassed heart region capable of releasing heart fluid from said fluid control device over a predetermined pressure, filling said bypassed heart region with heart fluid and allowing said heart to pump said heart fluid whilst in a bypassed condition, and whilst maintaining an inflow of heart fluid to said bypassed heart region.

34. A method of improving the removal of potential emboli from a bypassed heart region prior to the removal of said region from bypass including the steps of:
 connecting a fluid control device with an output portion of said bypassed heart region, said fluid control device having a predetermined pressure control device in communication with said bypassed heart region and being capable of releasing heart fluid from said fluid control device over a predetermined pressure;
 filling said bypassed heart region with heart fluid; and allowing said heart to pump said heart fluid whilst in a bypassed condition and whilst maintaining an inflow of heart fluid to said bypassed heart region.

\* \* \* \* \*

UNITED STATES PATENT AND TRADEMARK OFFICE
CERTIFICATE OF CORRECTION

PATENT NO. : 6,503,219 B2
DATED : January 7, 2003
INVENTOR(S) : Frederick Paget Milsom It is certified that error appears in the above-identified patent and that said Letters Patent is hereby corrected as shown below:

Column 13,
Line 28, delete "is." and insert -- is in --;
Line 29, delete "is" and insert -- in the --.

Signed and Sealed this

Twenty-first Day of September, 2004

JON W. DUDAS
*Director of the United States Patent and Trademark Office*